(12) United States Patent
Sarangan et al.

(10) Patent No.: US 8,481,768 B2
(45) Date of Patent: Jul. 9, 2013

(54) INTEGRATED PROCESS FOR THE PREPARATION OF FATTY ACID METHYL ESTER (BIODIESEL)

(75) Inventors: Swaroop Sarangan, Navi Mumbai Maharashtra (IN); Vidhya Rangaswamy, Navi Mumbai Maharashtra (IN)

(73) Assignee: Reliance Life Sciences Pvt. Ltd., Mumbai (IN)

( * ) Notice: Subject to any disclaimer, the term of this patent is extended or adjusted under 35 U.S.C. 154(b) by 1168 days.

(21) Appl. No.: 12/058,446

(22) Filed: Mar. 28, 2008

(65) Prior Publication Data

US 2008/0269513 A1    Oct. 30, 2008

(30) Foreign Application Priority Data

Mar. 30, 2007  (IN) ............................ 654/MUM/2007
Mar. 7, 2008   (WO) ................. PCT/IB2008/000128

(51) Int. Cl.
*C11B 1/00*     (2006.01)
*C09F 7/00*     (2006.01)

(52) U.S. Cl.
USPC ................................ 554/13; 554/16; 554/30

(58) Field of Classification Search
USPC ................................................ 554/13, 16, 30
See application file for complete search history.

(56) References Cited

U.S. PATENT DOCUMENTS

| 3,198,843 | A | * | 8/1965 | Barker | 568/869 |
| 4,623,489 | A | * | 11/1986 | Rivers, Jr. | 554/175 |
| 6,013,817 | A | | 1/2000 | Stern et al. | |
| 6,299,800 | B1 | | 10/2001 | Viswanathan | |
| 6,440,057 | B1 | | 8/2002 | Ergun et al. | |
| 6,713,117 | B1 | * | 3/2004 | Kodali | 426/601 |
| 6,822,105 | B1 | | 11/2004 | Luxem et al. | |
| 6,979,426 | B2 | | 12/2005 | Teall et al. | |
| 7,045,100 | B2 | | 5/2006 | Ergun et al. | |
| 7,087,771 | B2 | | 8/2006 | Luxem et al. | |
| 7,122,216 | B2 | * | 10/2006 | Copeland et al. | 426/417 |
| 7,126,032 | B1 | * | 10/2006 | Aiken | 568/869 |
| 7,666,234 | B2 | * | 2/2010 | Ghosh et al. | 44/308 |
| 2003/0201228 | A1 | * | 10/2003 | Chanrai et al. | 210/634 |
| 2005/0080279 | A1 | | 4/2005 | Barbieri et al. | |
| 2006/0260184 | A1 | | 11/2006 | Landano | |

FOREIGN PATENT DOCUMENTS

| EP | 806471 | * | 11/1997 |
| EP | 967264 | * | 12/1999 |
| GB | 760159 | * | 10/1956 |
| GB | 2159428 | * | 12/1985 |
| GB | 2159428 | * | 12/1996 |
| WO | WO 99/26913 | | 11/1998 |
| WO | WO 00/16492 | | 9/1999 |
| WO | WO 03/022961 | | 9/2002 |
| WO | WO 2006/043281 | | 10/2004 |
| WO | WO 2005063954 A1 | * | 7/2005 |
| WO | WO 2006043281 A1 | * | 4/2006 |
| WO | WO 2008/120223 | | 9/2008 |

* cited by examiner

*Primary Examiner* — Deborah D Carr
(74) *Attorney, Agent, or Firm* — Vinson & Elkins LLP (57) ABSTRACT

The disclosure provides methods and systems for the production of biodiesel from biological feedstocks such as vegetable oils or animal fats. In particular, the disclosure is directed to the product of biodiesel from seeds such as non-edible oil seeds. Methods for maximizing oil recovery from the feedstocks are provided, as well as methods to convert free fatty acids in the feedstocks into glycerides amenable to transesterification. Thus the methods and systems provide for efficient biodiesel production.

36 Claims, 10 Drawing Sheets

FIGURE 1

| Feed stock Type | Entry Section |
|---|---|
| Crude *Jatropha* Oil | Oil pretreatment |
| Refined Oil | Transesterification |
| High acidity oil / waste oil / used oil | Esterification / Glycerolysis |
| *Jatropha* oil seed | Seed Cleaning |
| *Jatropha* Seed Cake / Spent Bleaching Earth | Solvent Extraction Plant |

INTEGRATED PROCESS FOR THE PREPARATION OF FATTY ACID METHYL ESTER (BIODIESEL)

CROSS-REFERENCE TO RELATED APPLICATIONS

The present application claims the benefit of Indian Provisional Patent Application 654/MUM/2007, filed on Mar. 30, 2007, Indian NonProvisional Patent Application 654/MUM/2007, filed on Feb. 28, 2008, and International Patent Application PCT/IN2008/000128, entitled "An Integrated Process for the Preparation of Fatty Acid Methyl Ester (Biodiesel)", filed on Mar. 7, 2008, both of which are incorporated herein by reference in their entirety.

STATEMENT REGARDING FEDERALLY SPONSORED RESEARCH

Not applicable.

BACKGROUND OF THE INVENTION

Biodiesel is a petroleum diesel fuel equivalent that can be produced from a variety of biological sources including vegetable oils and animal fats. Because biodiesel's combustion profile is similar to that of petroleum diesel, it can be used in conventional diesel engines either alone or blended with traditional petroleum diesel. Given that biodiesel is a renewable fuel source with a significantly reduced environmental impact, it is extremely attractive as a replacement or adjunct to traditional petroleum diesel.

Unlike traditional petroleum diesel, biodiesel can be produced from entirely renewable sources: vegetable oils and animal fats. Consequently, biodiesel is a renewable energy alternative to petroleum diesel that is increasingly seen as a natural resource with a finite, limited supply. Moreover, even if biodiesel is not used as a complete replacement for conventional petroleum diesel, it may at least supplement or augment conventionally sourced petroleum diesel, stretching out those limited supplies.

Biodiesel is also attractive when compared to traditional petroleum diesel because of its significant environmental benefits. First, biodiesel is an essentially carbon neutral fuel. Unlike petroleum diesel which releases carbon that was previously stored or captured underground upon combustion, virtually all of the carbon that makes up biodiesel originates in the atmosphere and is simply returned to the atmosphere upon combustion. Second, biodiesel has a significantly improved emissions profile relative to conventional diesel. Carbon monoxide, particulate matter, sulfates, polycyclic aromatic hydrocarbons and unburned hydrocarbon emissions are all reduced by over 50% in biodiesel when compared to conventional diesel. Many studies do indicate, however, that nitrogen oxide emissions may be slightly increased in biodiesel.

Biodiesel can be produced from the fatty acid triglycerides present in vegetable oils and animal fats. The triglycerides are converted into mono alkyl esters of long chain fatty acids, such as fatty acid methyl esters and fatty acid ethyl esters.

There are three basic methods for the production of alkyl esters from vegetable oils and animal fats. The most prevalent method is base catalyzed transesterification with alcohol. The two other methods include conversion of triglycerides into alkyl esters using enzymes like lipase, and the use of solid catalysts like calcium aluminate and zinc aluminate. Advantages of the base catalyzed reaction include relatively low processing temperature and pressure; high conversion in a minimal time; direct, single step conversion to methyl ester with no intermediate reactions; and a relatively simple reaction apparatus.

Given the relative ease of production of biodiesel, along with its renewable and environmentally friendly characteristics, biodiesel is a very attractive alternative energy source, and worldwide production of biodiesel has increased dramatically in recent years. In the United States, for example, production of biodiesel increased over ten fold from approximately 20 million gallons to 250 million gallons in the three year period from 2003 to 2006. These significant increases in production have resulted in an increased demand for biodiesel feedstocks worldwide.

Feedstocks for biodiesel include virtually any vegetable oil or animal fat. Soybean oil is the primary biodiesel feedstock, currently accounting for some 90% of biodiesel production worldwide. Other vegetable oils, such as corn, cottonseed, canola or rape seed, flax, sunflower and peanut, also are used, but these seed oils are generally more expensive than soybean oil. Moreover, the use of such edible oils for the production of fuel competes with their historical use in the food supply, raising concerns over future supply and costs as biodiesel feedstock demand continues to increase.

Because the use of edible oils as biodiesel feedstocks competes with their human consumption, other non-edible oil sources are particularly attractive for potential use as biodiesel feedstocks. Various types of non-edible oil bearing trees like *Jatropha curcas* are being cultivated in large scale for use as biodiesel feedstock. It is imperative, therefore, to develop a processing scheme that extracts the maximum amount of biodiesel from such non-edible sources.

Animal-derived products such as tallow, choice white grease or lard, poultry fat and yellow grease also contain triglycerides and are used as feedstocks. These products, when compared to plant-derived oils, often offer an economical advantage as a feedstock. There is also some preliminary indication that biodiesel from these sources, which are high in saturated fats, produces less nitrous oxide than biodiesel produced from plant oils.

The third main source of triglycerides is recycled oil and grease that can be obtained from restaurants and food processing plants. Although these recycled oils require more pre-treatment than is required for virgin vegetable oils, the use of a recycled product such as used cooking oil solves waste disposal problems and is economically attractive.

Although a number of approaches have been, and continue to be experimented with, the industry has still not been very successful in developing an economically viable biodiesel fuel which also meets the necessary quality standards.

WO 2006/043281 describes a process of chemical neutralization of seed oil, including from *Jatropha curcas*, and sending the by-product for soap making. It is well known that there is considerable loss both in terms of fatty acid and oil carry over by this method, thus limiting the yield and increasing the processing cost of oil. Also the oil expelling technique used in this method is energy intensive and leaves behind over 8% of the otherwise available oil in the seed cake. These less efficient approaches result in increased biodiesel production costs.

WO 2006/016492 describes a process of degumming and transesterification of oil to produce biodiesel. The disadvantage of carrying forward a simple degummed oil is that it allows heavy metals and other finely suspended matter in the final product, which may require high levels of stabilizers to preserve oxidation stability.

U.S. Pat. No. 6,399,800 suggests esterification of a dried, saponified feedstock as a process to convert fatty acids into fatty acid alkyl esters. This involves capital intensive special reactors, and requires a complex process to eliminate moisture from the saponified feedstock.

High levels of free fatty acids, which are often present in crude, old, or reused oils, can inhibit the catalysts used in conventional transesterification reactions. U.S. Pat. Publication No. 20050080279 provides a different way of handling oil with high free fatty acid content. The disclosure requires large amounts of glycerin to be used in the process, which requires equipment with greater capacity, and the disclosure also involves a more energy intensive process to obtain the correct yield.

U.S. Pat. Nos. 7,087,771 and 6,822,105 primarily address only the soap stock produced as a transesterification by-product, and do not explain forward or backward integration with all of the steps of the process from seed to biodiesel.

U.S. Pat. No. 6,013,817 describes a process wherein both the oil and free fatty acids are transesterified, resulting in not only greater throughput, but also greater catalyst consumption. Further, the process also requires reprocessing the soap stock formed of entire fatty acids back to glycerides. This again requires a time-consuming and lengthy process, larger equipment and greater processing costs due to multiple processing of same material.

U.S. Pat. No. 6,979,426 provides a modular biodiesel production unit with all of the necessary components incorporated onto one platform for ease of relocation. The modular production unit includes a mixing unit, a reactor unit, a separation unit, a distillation unit, and a filtering unit, all incorporated onto or into a self-contained platform or housing that is able to be easily relocated. This system does not, however, allow for fatty acid/soap stock recycling which is able to increase the yield of biodiesel.

PCT application WO 1999/026913 relates to a method and equipment for producing biodiesel economically in large-scale industrial equipment. However, this patent application does not deal with an integrated plant or process beginning with oil bearing seeds as a feedstock.

PCT application WO 2003/022961 relates to machinery for biodiesel production wherein specialized reaction tanks with vertical rotating feed tubes having separators, and inlet and outlet openings are used. The machinery occupies minimal plant space; minimal on-site feedstock; and minimal on-site storage. Again, there is no integration of seed processing to this system, resulting in lower overall yield of biodiesel from a given amount of seed.

U.S. Pat. Publication No. 20060260184 includes a method and apparatus for the production of biodiesel fuel, which includes a compact processor including a vapor recovery system for removing excess alcohols from the fuel and an additional chemical cleaner. However the publication does not address the recycling of by-products and waste to increase biodiesel yield.

Recently, ultrasonic reactors have been employed to dramatically speed up the transesterification reaction time. These reactors also have reduced amounts of catalysts required for the reaction, and result in better separation of the phases. Nonetheless, this ultrasonic approach is still relatively expensive.

Thus, there is a need in the art to be able to efficiently and inexpensively produce biodiesel from a variety of feedstocks including, in particular, inedible seed oils. Additionally, further processing of the by-products and intermediates of the production process itself, like the seed cake, crude oil, acid oil, spent bleaching earth, and soap stock, may also lead to the recovery of additional oil for transesterification. Finally, there is also a need for modular equipment for all of these processes which can be easily scaled up for large scale production of biodiesel.

SUMMARY OF THE INVENTION

The present disclosure provides a method for producing oil suitable for use in producing fatty acid alkyl esters from seeds. The method comprises cleaning the seeds; cracking the seeds; softening the seeds; extracting oil from the cracked, softened seeds, leaving a residual seed cake; extracting oil remaining in the residual seed cake with a solvent; and collecting the oil extracted from the cracked, softened seeds and the residual seed cake.

In preferred embodiments, the seeds are inedible oil seeds, for example, seeds of *Jatropha curcas*. In certain embodiments, the seeds may be from soybean, canola, castor, coconut, corn, cotton, flax, hemp, jojoba, mustard, sunflower, pongamia, copaiba, safflower, sesame, candlenut, petroleum nut, or neem.

In certain embodiments, the seeds may be softened by steaming, and in some embodiments, steaming for at least 90 minutes. The steaming may heat the seeds to a temperature of up to about 70° C.

In other embodiments, the oil may be extracted from the cracked, softened seeds in an oil expander. The expander may operate under high pressure, for example at about 140° C.

In preferred embodiments, the solvent used to extract the oil is hexane.

In certain embodiments, the extracted oil may be separated from the solvent in a flasher separator. In other embodiments, the collected oil may be degummed and bleached. The oil may be bleached with bleaching earth, and oil may be recovered from the bleaching earth after bleaching.

In certain embodiments, the extracted oil may be deaerated and deodorized. In other embodiments, the extracted oil may be refined.

In preferred embodiments, the extracted oil is used for the production of fatty acid alkyl esters, which may, in certain embodiments, be produced by a transesterification reaction.

The present disclosure also provides a method for producing fatty acid alkyl esters from oilseeds. The method comprises a combination of any of the following steps: (a) cleaning oilseeds; (b) cracking the oilseeds; (c) softening the cracked oilseeds by steaming; (d) extracting oil from the cracked, softened seeds, leaving a residual seed cake; (e) extracting oil remaining in the residual seed cake with a solvent; (f) collecting the oil extracted from the cracked, softened seeds and the residual seed cake; (g) degumming the collected oil; (h) bleaching the degummed oil; (i) recovering bleaching earth used during bleaching and extracting oil from the used bleaching earth with a solvent; (j) refining the bleached oil by distillation to remove free fatty acids from the oil; (k) transesterification of the refined oil and the monoglycerides, diglycerides and triglycerides produced by glycerolysis to produce fatty acid alkyl esters and crude glycerin; (l) glycerolysis of the free fatty acids removed from the oil during refining with crude glycerin produced from the transesterification process to produce monoglycerides, diglycerides, and triglycerides; (m) separating the fatty acid alkyl esters and the glycerin produced by the transesterification reaction.

In preferred embodiments, the oilseeds are inedible oilseeds, and more preferably, seeds of *Jatropha curcas*. In other embodiments, the oilseeds may be from soybean, canola, castor, coconut, corn, cotton, flax, hemp, jojoba, mustard, sunflower, pongamia, copaiba, safflower, sesame, candlenut, petroleum nut, or neem.

In certain embodiments, the transesterification reaction may further comprise contacting the refined oil and monoglycerides, diglycerides and triglycerides with an alcohol and a base. The alcohol used may be, for example, methanol, and the base may be, for example, sodium hydroxide, potassium hydroxide, or sodium methoxide.

In certain embodiments, the transesterification reaction may further comprise a first and second round of transesterification, wherein at least some of the glycerin produced in the first round of transesterification is removed prior to the second round of transesterification.

The disclosure also provides a method for purifying and reusing crude glycerin produced in a transesterification reaction, comprising: (a) obtaining crude glycerin produced by a transesterification reaction, wherein the crude glycerin comprises glycerin, alcohol, and free fatty acid; (b) removing at least some of the alcohol from the crude glycerin by a first flash distillation; (c) separating at least some of the free fatty acid from the crude glycerin; and (d) using the crude glycerin in a glycerolysis reaction to produce monoglycerides, diglycerides, and triglycerides from free fatty acids.

In preferred embodiments, a second flash distillation to remove additional alcohol follows separation of the free fatty acid from the crude glycerin. In other embodiments, the glycerolysis reaction is contacted at a temperature between about 100° C. and 200° C. In preferred embodiments, the monoglycerides, diglycerides, and triglycerides from the glycerolysis reaction may be combined with additional triglycerides. In certain embodiments the additional triglycerides may be from vegetable oils or animal fats. In other embodiments, the combined monoglycerides, diglycerides, triglycerides and additional triglycerides are used for the production of fatty acid alkyl esters.

The present disclosure also provides a method for recovering oil from spent bleaching earth, comprising: (a) extracting used bleaching earth with a solvent, wherein the used bleaching earth comprises triglycerides from vegetable oils or animal fats; (b) volatizing the solvent and triglycerides; and (c) removing at least some of the solvent from the triglycerides in a flasher separator. In certain embodiments, the triglycerides are used to produce fatty acid alkyl esters, for example, through a transesterification reaction.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

The term "biodiesel" as used herein refers to any mono alkyl esters of long chain fatty acids produced from biological feedstocks such as vegetable oils or animal fats, or other feedstocks. Representative fatty acid mono alkyl esters include fatty acid methyl esters and fatty acid ethyl esters.

The term "feedstock" as used herein refers to any biological source of triglycerides such as vegetable oils or animal fats. Exemplary feedstocks include but are not limited to: plant oils from soybean, canola, castor, coconut, corn, cotton, flax, hemp, jatropha, jajoba, mustard, sunflower, pongamia, copaiba, safflower, sesame, candlenut, petroleum nut, and neem; and animal fats including but not limited to tallow, lard, yellow grease, and chicken fat. In addition, waste oils from food processing, crude oil, acid oils from oil refineries, spent bleaching earth, and soap stocks produced from the neutralization of food oils may be used as feedstocks.

The term "yield of biodiesel" as used herein refers to the quantity of biodiesel produced from a given quantity of oil or fatty acid input.

The present disclosure provides a low cost method for the production of biodiesel using modularly expandable equipment and components, and yielding maximum fatty acid methyl esters. In addition, biodiesel produced according to the present disclosure meets the international quality standards established for biodiesel. The present disclosure also provides for the production of biodiesel from multiple feedstocks, and, in particular, provides methods for extraction of crude oil from non-edible oil seeds such as *Jatropha curcas* and the like; followed by conversion to free fatty acid and then esterification. Finally, the present disclosure also provides methods for maximum oil extraction, pretreatment of the oil, processing the by-products and waste generated by the process such as spent bleaching earth and the free fatty acid obtained after physical neutralization of soap stock to extract more glycerides.

The steps involved in an embodiment of the present disclosure, from seed to biodiesel, are: (1) pretreatment of the seed; (2) extraction of seed oil by expanding and/or expelling; (3) recovery of additional oil from the seed cake by solvent extraction; (4) pretreatment of the extracted and recovered oils, such as oil and seed cake oil; (5) refining the oil; (6) recovery of oil from spent bleaching earth by solvent extraction; (7) transesterification; (8) glycerolysis; (9) recovery of additional triglycerides from the soap stock; (10) glycerin recovery; (11) methanol recovery; and (12) analysis of the final biodiesel product.

Significantly, the above process contains additional processing for the waste and by-products of the oil expanding/expelling, oil refining and transesterification steps. Through additional processing of the seed cake left over after oil expelling, the spent bleaching earth used in refining, and of the soap stock remaining after transesterification, those waste products are recycled to extract additional triglycerides that would otherwise be lost during the production process. Given this processing approach, the yields of biodiesel from oil seeds can be maximized.

Seed Pretreatment

When the initial feedstock into the system is a seed, the seeds are first cleaned to remove any extraneous matter or debris. Cleaning may be done by sifting or sieving, and manually or automatically selecting the seeds. The seeds are then crushed or cracked open, for example by passing the seeds through a seed cracker, in which a corrugated roller crushes or cracks the seeds open. The crushed or cracked seeds are then cooked with steam at given temperature depending on the seeds for given length of time for softening. The parameters are controlled either manually or automatically. The steam cooker is a multi-staged vertical vessel with steam heated bottom plates and specially designed for live steam injection to obtain uniform heating of material. The agitator is designed to move the material from one stage to another. Automatic controls to make level adjustments and regulate the flow are also provided.

Preparation of the seeds prior to extraction is critical to obtain the best results for solvent extraction. The particle size of the crushed seeds must be such that the solvent can reach the core, but yet not so fine that it leads to percolation and channeling effects.

The cracked and cooked seeds are then flaked in a flaker. The flaking process breaks down the cellular structures of the seeds and exposes a larger surface area for efficient oil extraction. In this process, the material is passed through two rollers where the gap is suitably adjusted by a hydraulic device to obtain flakes of 0.25 to 0.3 mm thickness and pre-conditioned to have 8 to 10% of moisture content.

Oil Extraction

Oil is extracted from the softened seeds, for example, by passing the seed flakes though an oil expander at high pressure to expel oil from the seeds. The expander is a high shear machine which shears the oil cells down, making solvent extraction of the seed cake easier. The seeds pass through the expander for a short period of time, ranging from 15 to 22 seconds, depending on the material. The expander is heated to nearly 140° C. The high temperature contact lasts only for a few seconds, which on discharge, flashes moisture. The expander process leads to easier solvent extraction of the seed cake and also improves the quality of oil produced by solvent extraction.

At the outlet of the expander, some oil is collected from the seeds and then sent for pretreatment and refining. The amount of oil extracted could vary depending on the type of oil seeds.

Seed Cake Solvent Extraction

Additional oil may be recovered from the seed cake left over from the oil expelling step. Similarly, oil may be recovered from spent bleaching earth used in the oil pretreatment step. Spent bleaching earth and the residual seed cakes may be initially processed by a cake breaker and roller mill. Two spiked rolls break the large pieces of cake into smaller ones, which are further broken down in the roller mill to required size. After processing in the cake breaker and roller mill, oil may be recovered from the spent bleaching earth and seed cakes by solvent extraction. A solvent of choice is hexane. However, other solvents like polar solvents and chlorinated solvents may be used depending on the seeds.

Pretreatment of Collected Oil collected from both the initial oil expelling and from the solvent extraction of the seed cake and spent bleaching earth may go through additional pretreatment before physical refining. Pretreatment may include degumming and bleaching. Degumming is especially necessary if large amounts of phosphatides are present in the oil feedstock. Degumming may be accomplished by acidifying the feedstock. Bleaching further purifies the oil and is typically done by mixing the oil with bleaching earth, sometimes known as bentonite, Fuller's earth or acid activated earth, for example. The bleaching earth absorbs impurities from the oil and is further recycled in the process. The amount of earth used may vary depending on oil condition, and it may go up to 2% (w/v) at max. Normally, the oil is dehydrated under vacuum and contacted with the earth to remove colouring pigments, fine sediments and some heavy metals. After the bleaching process, the earth may be filtered out and sent back to extract residual oil in the spent earth, as described above. It may contain about 14 to 18% (v/w) of oil in it.

Refining of Oil

The pretreated oil may next be refined before sending to the transesterification reaction. Refining may include deaeration and moisture removal steps. Refining may also include a distillation step to remove free fatty acids from the triglycerides. The oil is deodorized at about 250° C. at 2 torr pressure in a vessel containing three to four trays allowing the oil to be maintained at the same uniform temperature and vacuum throughout the entire process. The oil is stripped with a small quantity of live steam injected into the trays, stripping out the fatty acids and other volatile materials from the oil. The deodorized oil may then be passed through a series of heat exchanging devices to transfer about 85 to 88% of its heat to incoming oil. The fatty acid collected in a scrubber is fed to the glycerolysis section to convert it into glycerides while the oil is taken for transesterification.

Glycerolysis

Free fatty acid collected from the crude oil is sent for glycerolysis. In glycerolysis, glycerin, also commonly referred to as glycerine or glycerol, is added to the free fatty acids with a catalyst and incubated around 200° C. under a very high vacuum. This process converts free fatty acids to monoglycerides and other glycerides that can then be transesterified, along with the oil triglycerides, to biodiesel with a base catalyst.

Transesterification

The triglycerides of the refined oil, as well as the glycerides from the glycerolysis reaction, are converted into fatty acid alkyl esters via a transesterification reaction. Transesterification may be accomplished in several different ways that are well known to those of skill in the art, but the most common approach is a base catalyzed reaction, in which the oils are reacted with an alcohol, most commonly methanol or ethanol, in the presence of a base catalyst, most commonly sodium hydroxide, sodium methoxide, or potassium hydroxide. The reaction incubates at just over the boiling point of the alcohol used and under slight pressure.

Transesterification may also be accomplished enzymatically using the enzyme lipase. In such enzyme catalyzed reactions, the oil is combined with an excess of alcohol, again typically ethanol or methanol, and the lipase enzyme catalyzes the transesterification reaction between the oil triglycerides and the alcohol. An example of lipase catalyzed transesterification of *Jatropha* oil may be found in Shah et al., "Biodiesel preparation by lipase-catalyzed transesterification of *Jatropha* oil." Energy and Fuel 15:154-159 (2004).

The predominant products of the transesterification reaction are simply the biodiesel fatty acid alkyl esters and glycerin. Because the glycerin phase is denser than the biodiesel phase, the products may be separated by gravity separation or centrifugation.

Glycerin Purification

The raw glycerin by-product of the transesterification product frequently contains excess alcohol that can be captured and recycled. The glycerin may be heated and flashed to remove the excess alcohol, and the evaporated alcohol may then be collected for additional processing.

Because the transesterification reaction occurs at a basic pH, the glycerin may also be neutralized before it is further processed. The glycerin may be neutralized with HCl or any other appropriate acid known in the art. The purified glycerin may be recycled back into the production process in the glycerolysis step, where it is used in the conversion of free fatty acids into monoglycerides and diglycerides, which are then amenable to transesterification.

Additional methods for the purification of glycerin produced from a transesterification reaction may be found in U.S. Pat. No. 7,126,032 to Aiken, for example, which is incorporated herein by reference.

Methanol Recovery

Excess methanol collected from the transesterification reaction and the glycerin purification process may be further processed, allowing the methanol to be recycled. Distillation is a common approach to purification of the methanol, which may be employed for recycling.

Analysis of the Final Biodiesel Product

Several national and international standard setting organizations have set standards for biodiesel. For example, the American Society for Testing and Materials issued a standard for biodiesel as ASTM D6751. Common European standards for biodiesel include EN 14214 and DIN 51606. These standards set out various specifications and parameters for biodiesel, for example, the sulfur content, flash point, and oxidation stability, which biodiesel produced under the standard must meet. In addition, the standards specify the tests and procedures that must be used in making these determinations. Following production, the biodiesel may be analyzed according to these procedures to verify that it meets the standards.

The following units, which are easily expandable and installed, may be included in the disclosed process:
  Seed pretreatment unit/oil expander
  Solvent extraction unit with facility of solvent recovery
  Pretreatment of oil unit
  Oil refining unit
  Glycerolysis and transesterification unit
  Recovery units The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Seed Pretreatment and Oil Extraction

Figure 1:
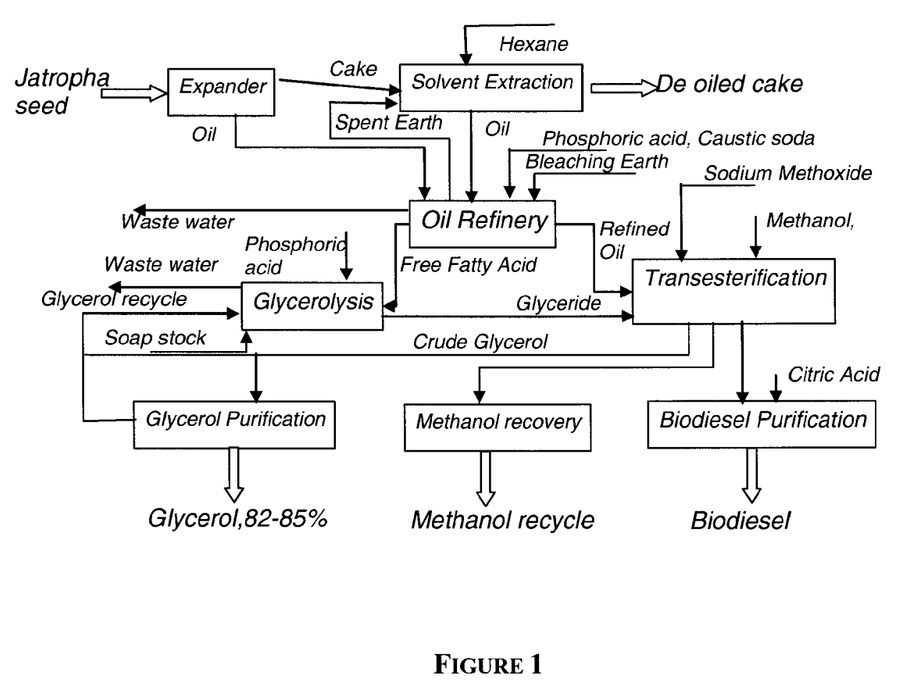
FIG. 1: The integrated biodiesel process.
Figure 2:
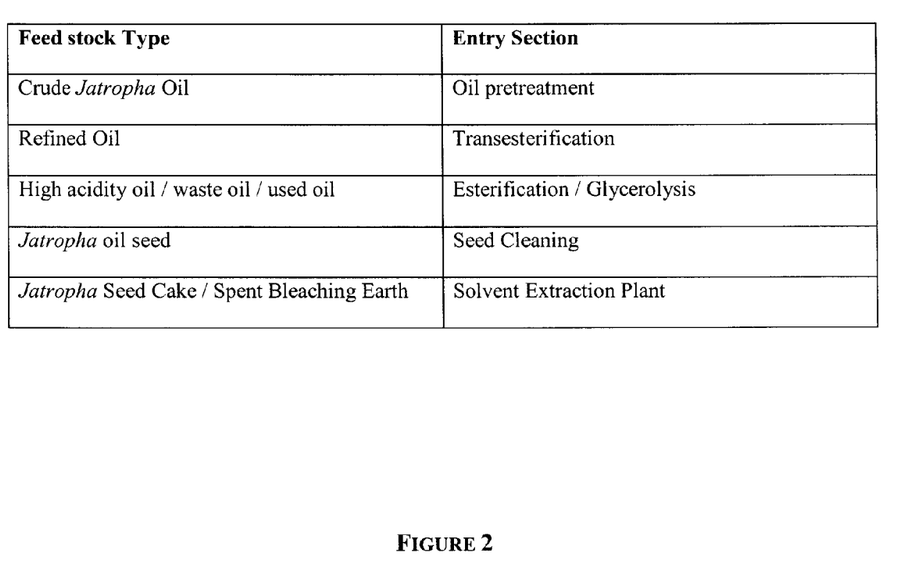
FIG. 2: The multiple feedstock entry points in the process.
Figure 3:
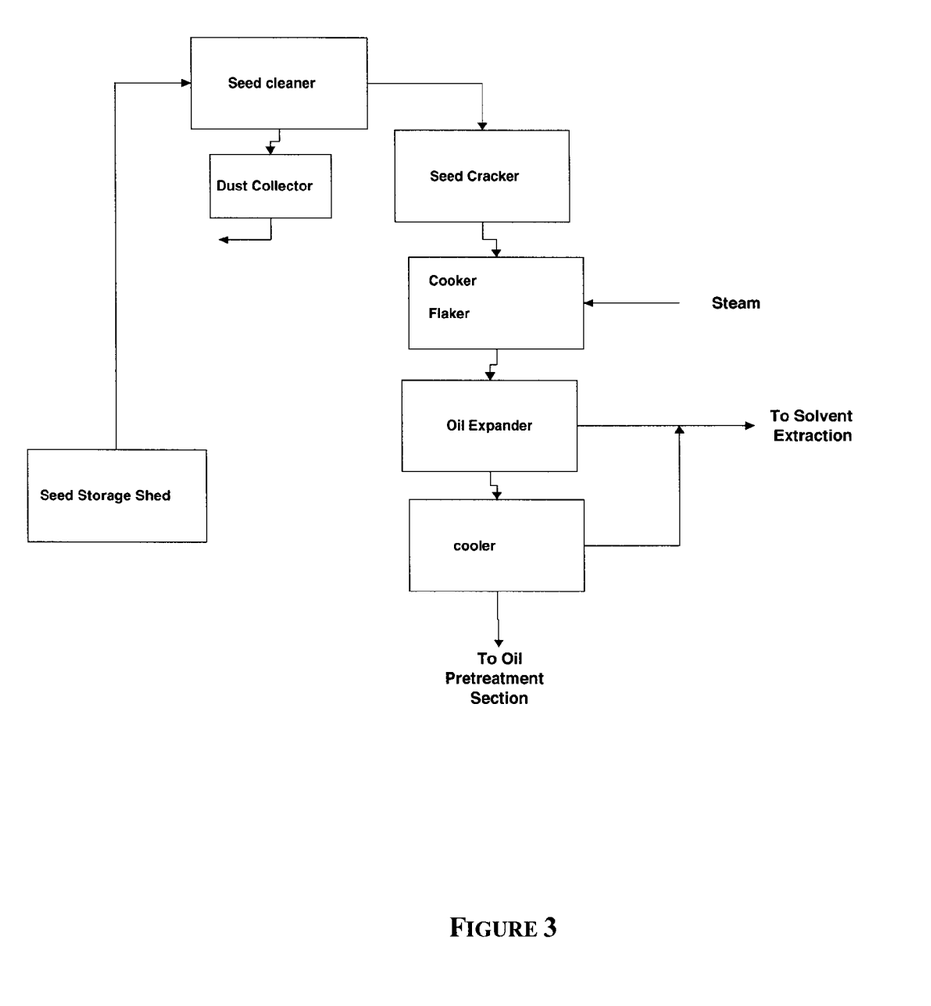
FIG. 3: The oil extraction process by the oil expander.

*Jatropha* seeds from a storage shed were fed into a seed cleaner by bucket elevators. The seed cleaner, comprising sieves and magnetic devices, is used to remove all foreign matter from the seeds. The cleaned seeds were then fed to the seed cracker, where corrugated rolls cracked the *Jatropha* seeds into a suitable size. The cracked seeds were then cooked in a steam cooker at about 70° C. for about two hours, to facilitate easy and efficient extraction of oil. The cooked seeds were then flaked to 0.25 to 0.35 mm size and passed through an oil expander at high pressure lasting for a few seconds to 22 seconds at about 140° C. maximum. The expander sheared and squeezed the flakes to pressures exceeding 100 kg/sq.cm, thereby expelling the first oil fraction from the seeds. The expelled oil was collected and sent to the oil pretreatment section, while the seed cake remaining from the oil expander was sent to the solvent extraction section. A schematic of the seed cleaning and oil extraction process may be seen in FIG. 3.

Example 2

Solvent Extraction and Solvent Recovery System

Figure 4:
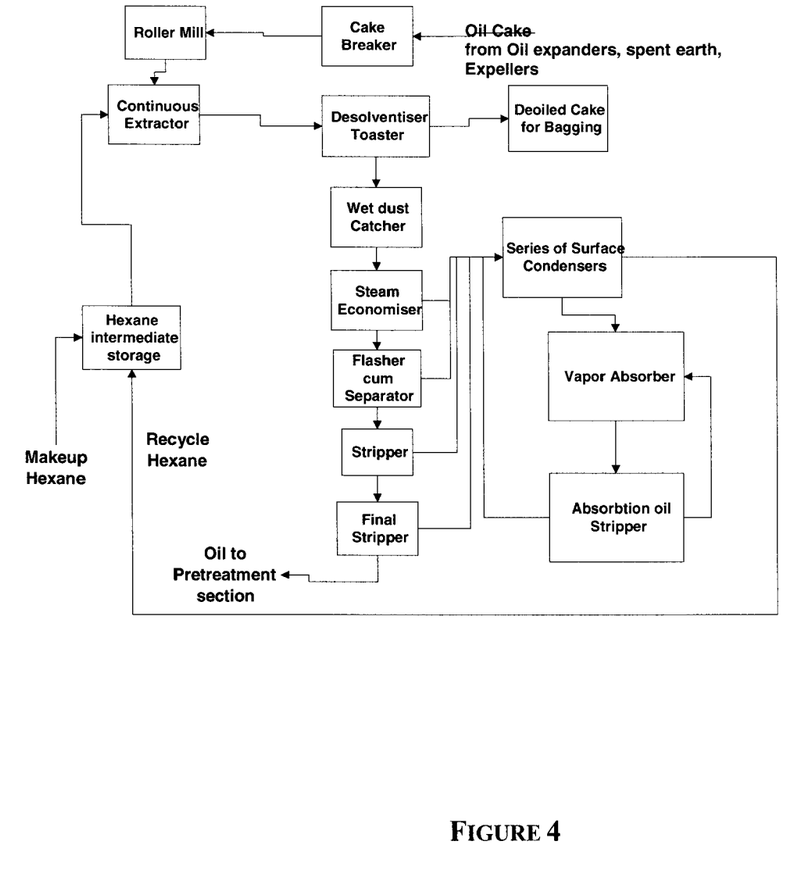
FIG. 4: Solvent extraction plant to obtain residual oil from seed cake and spent bleaching earth.

The seed cake from the oil expander and the spent bleaching earth from the refining section were passed through a cake breaker and roller mill before conveying it to the continuous extractor, where the leftover oil in the seed cake was extracted with the solvent hexane. The hexane was added to the seed cake by spraying the seed cake as it moved along on a solvent tight conveyer. The mass was then sent to the Desolventiser Toaster, where de-oiled cake was separated and discharged for bagging. The volatized oil and solvent went from the Desolventiser Toaster through various heat recovery exchangers and was then flashed in a flasher separator to separate the oil and solvent. The recovered oil was passed through two strippers to remove residual hexane, and the hexane-free oil was then sent to the oil pretreatment section after cooling. The hexane vapors were condensed through a series of surface condensers, and finally, residual vapors were absorbed in a vapor absorber. A schematic of solvent extraction from the seed cake and spent bleaching earth is shown in FIG. 4.

Example 3

Figure 5:
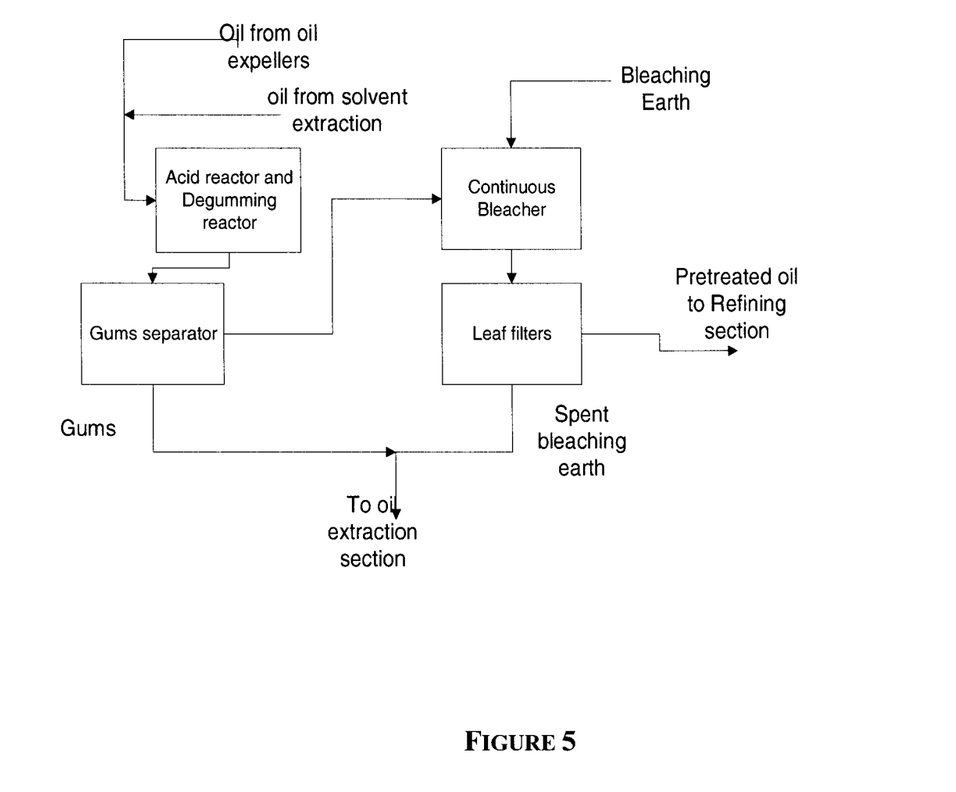
FIG. 5: Oil refining process comprising degumming and bleaching steps.

Pretreatment of Oil collected from the oil expeller and solvent extraction was pretreated by degumming and bleaching before further processing. The collected oil was mixed with phosphoric acid in an acid reactor at about 80° C. and held for about 30 minutes. This was followed by caustic addition and hot water washing of oil at a temperature of 75° C. Next, the gums were removed in a centrifugal separator. The degummed oil was then sent to a continuous bleacher where bleaching earth was added. After bleaching, the mixture was passed through pressure leaf filters to separate out the spent bleaching earth from the bleached oil. This bleached oil was then sent to the oil refining section, and the spent bleaching earth was returned back to the solvent extraction plant for removing residual oil. A schematic of the pretreatment phase is shown in FIG. 5.

Example 4

Refining of the Oil

Figure 6:
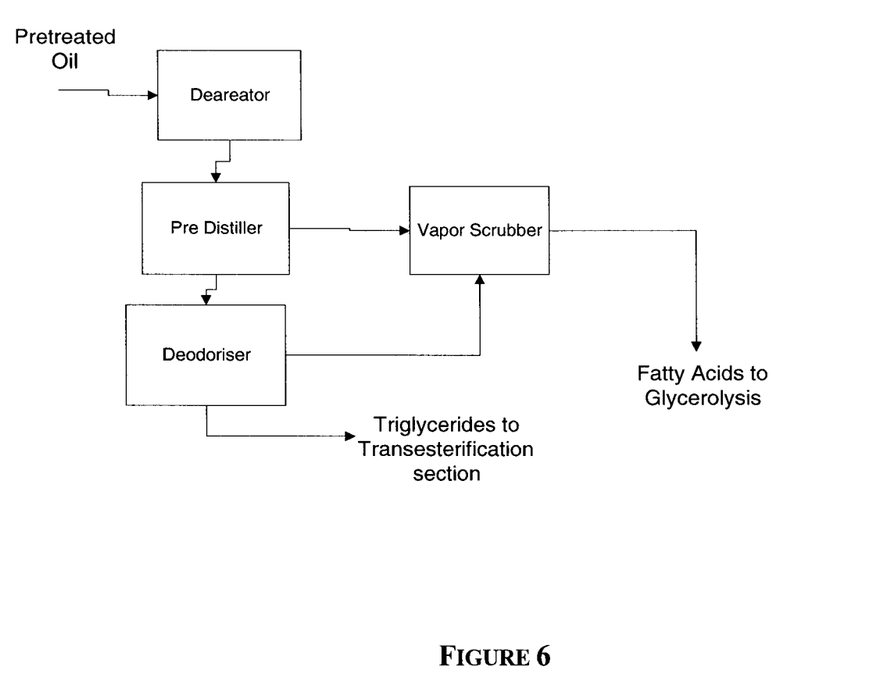
FIG. 6: Physical refining process of bleached oil.

After passing through a series of heat exchangers, the pretreated oil was fed into a deaerator for deaeration and moisture removal. The deaerated oil was then sent to a pre-distiller to distill out free fatty acids before sending it to the deodorizer. The pre-distiller and deodorizer were operated under 2 torr vacuum created by steam ejectors and about 250° C. The oil is stripped with open live steam to remove volatile matters including free fatty acids. The distilled, deodorized oil was collected for transesterification, while the condensate, comprising free fatty acids, was collected for glycerolysis. The oil had free fatty acid content less than 0.1% (w/v), soap content of less than 2 p.p.m., and moisture content less than 0.05% (v/v). A schematic of the refining process is shown in FIG. 6.

Example 5

Glycerolysis

Figure 7:
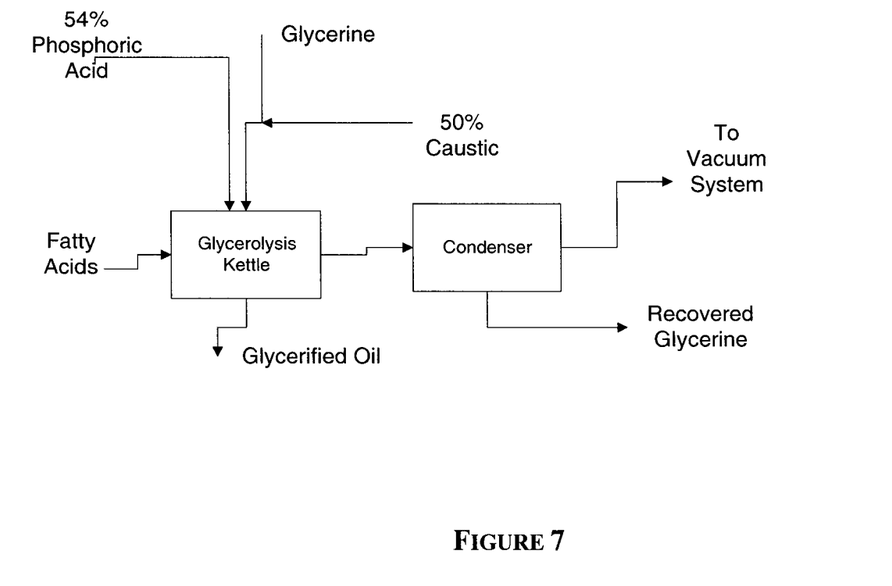
FIG. 7: Conversion of waste oils rich in free fatty acids to glycerides.

In this step, the free fatty acids obtained from the refining process and the soap stock by-product of the transesterification process were reacted with glycerin (both crude and refined from the biodiesel production process) in the presence of a catalyst, 0.5% phosphoric acid. The reaction was carried out between 121° C. to 185° C. under high vacuum of about 1 torr with intense agitation. Glycerin converted to glycerified oil or into glycerides by this process was used for transesterification as described below. A schematic of the above process is shown in FIG. 7.

Example 6

Transesterification

Figure 8:
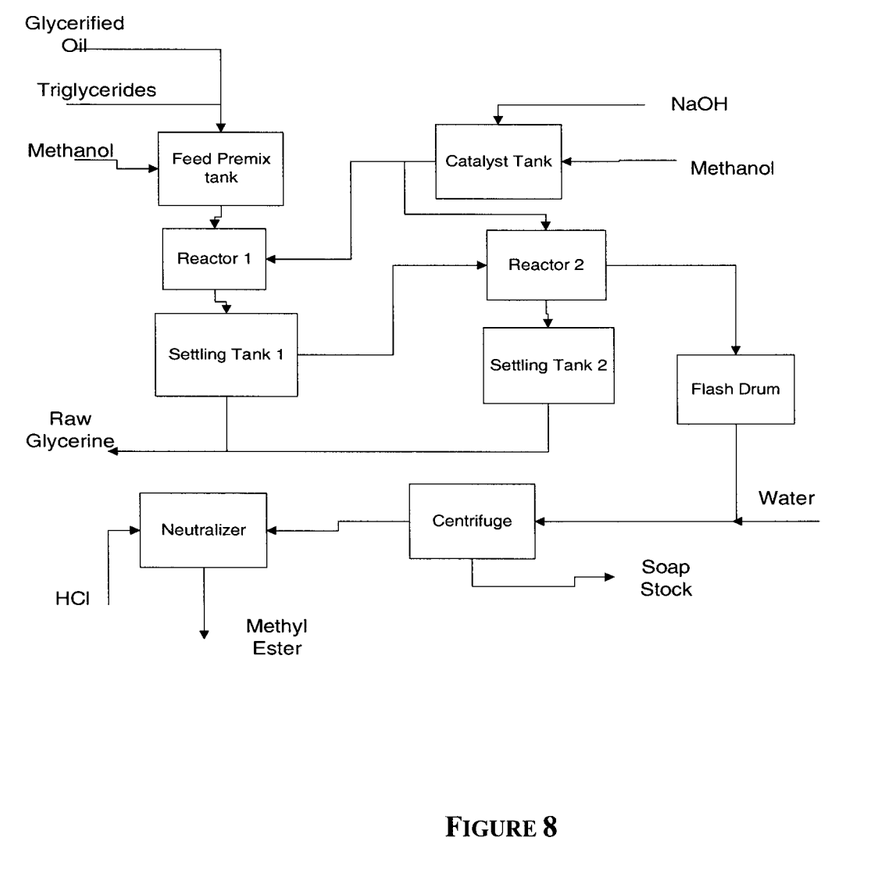
FIG. 8: Transesterification process to convert oil to fatty acid methyl ester, or biodiesel.

Refined oil triglycerides, as well as glycerified oil products from the glycerolysis process, were first mixed with methanol (volume of 1.5:1 (v/v)) in a premixing tank and then fed into the first transesterification reactor. Sodium methoxide was added as the catalyst of less than 0.1% (w/w). The reactor was maintained under a vacuum and the reaction temperature was maintained by steam heating coils. The pressure was initially a mild vacuum to remove moisture, and then normal pressure during the reaction, with temperatures about 65° to 68° C. for about 70 to 80 minutes duration.

The transesterification product was sent to the settler, where the glycerin by-product was removed. The biodiesel product (fatty acid methyl esters), along with excess methanol and unreacted oil, were fed into a second transesterification reactor for reaction completion. After the second round of transesterification, glycerin by-product was removed in a settling unit as above, combined with glycerin from the first transesterification reaction and sent for purification and methanol recovery as described below. The biodiesel methyl esters were collected, heated, and flashed to vaporize excess methanol at slightly above methanol vaporization point, around 75° C. Methanol condensate was then recirculated into the premixing tank for use in additional transesterification reactions.

Methyl ester collected from the flasher was washed with water (15% of ester volume) under agitation in a reactor and centrifuged to remove residual soap stocks. Following centrifugation, the pure methyl ester was neutralized with HCl as required. Optionally, commercially available magnesium silicate of about 2% was used with ester and heated to 75-80° C. and held for about 75 minutes. The collected methyl ester was then filtered to remove ester and solids separately in a filter press. A complete schematic for the transesterification process is shown in FIG. 8.

Example 7

Glycerin Purification

Figure 9:
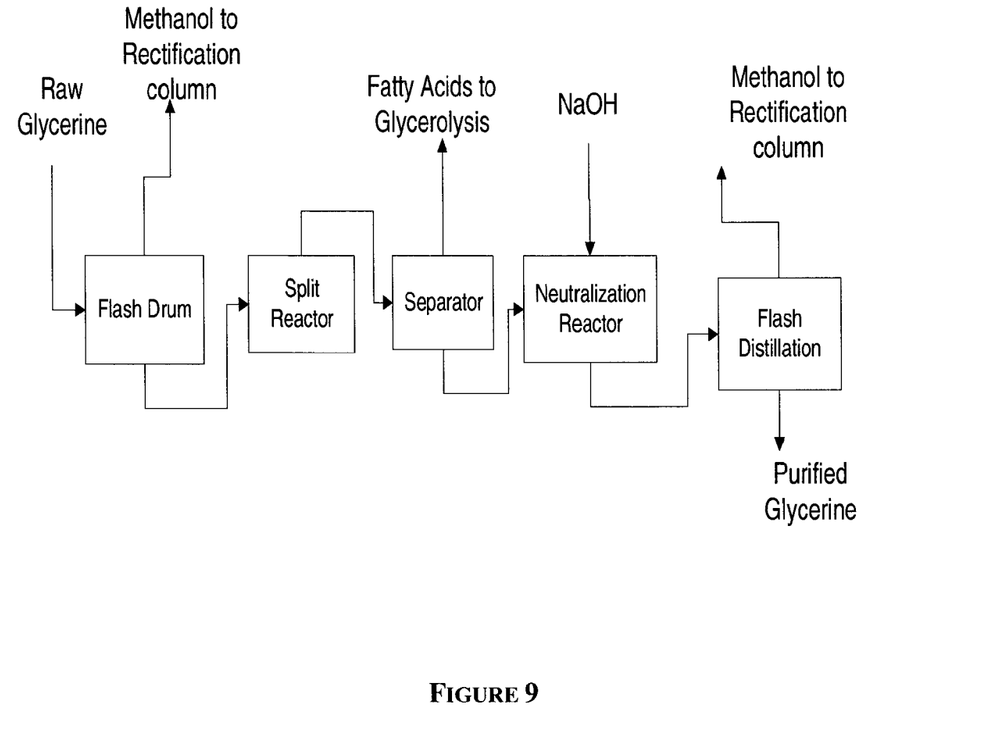
FIG. 9: The glycerin purification process.

Raw glycerin from the transesterification reaction was heated and flashed in a flashing drum to vaporize excess methanol remaining after transesterification. The evaporated methanol was collected and sent to the methanol recovery unit. Glycerin recovered from the flashing drum was acidified with HCl and fed into the split reactor. Effluent from the split reactor was sent to a separator unit where the glycerin was separated from free fatty acids. Free fatty acids collected from the separator were recycled into the glycerolysis process.

Glycerin from the separator was neutralized with base— caustic soda solution of 50% concentration and flash distilled again to remove any residual methanol, yielding purified glycerin. The residual methanol with the methanol collected from the first flashing was sent to the methanol recovery unit. A schematic of the process is shown in FIG. 9.

Example 8

Methanol Recovery

Figure 10:
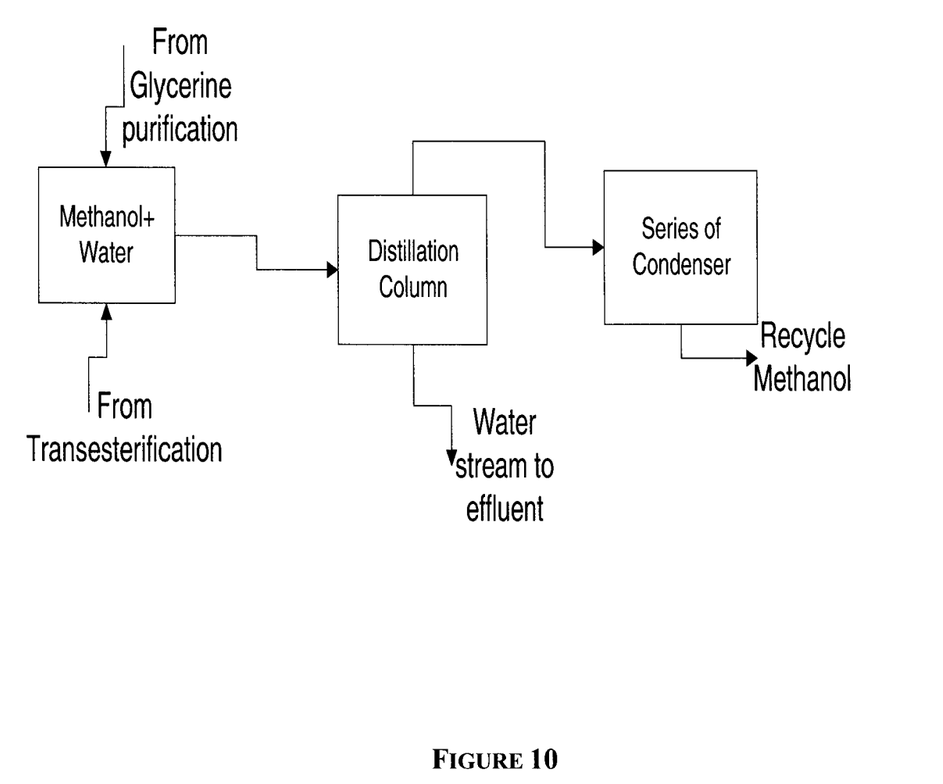
FIG. 10: The methanol recovery process.

Excess methanol collected from the transesterification reaction and the glycerin purification process was further processed so that they could be recycled for additional transesterification reactions. The collected methanol was passed into a distillation column and heated above its boiling point. Vaporized methanol from the top of the distillation column was condensed over a series of condensers, the final one being chilled with 10° C. water and the purified methanol condensate was recycled into the transesterification reaction. A schematic of the process is shown in FIG. 10.

Example 9

Biodiesel Analysis and Yield Calculation

The fatty acid methyl ester produced from this process was analyzed according to the testing procedures prescribed by EN 14214 and ASTM D6751 and found to conform to the standards.

A mass balance for the production process is shown below in Table 1. From an initial input of 3,330 kg of *Jatropha* seeds, this process produced 1014 kg. Considering that the oil content of *Jatropha* seeds is 30%, the yield of biodiesel to seed oil input was 1.015. The additional biodiesel production, over the original oil content of the *Jatropha* seed, may be attributed to the free fatty acid content of the seeds.

TABLE 1

Mass balance for the *Jatropha* seed biodiesel production process.

| Description | Quantity | Unit | Remarks |
|---|---|---|---|
| Oil content in *Jatropha* seed | 30 | % | |
| *Jatropha* seed quantity | 3330 | Kg | |
| Oil extracted by oil expander/expeller | 590 | Kg | |
| Seed cake taken to solvent extraction | 2740 | Kg | |
| Input to solvent extraction section, Including recycling of spent bleaching earth | 2765 | Kg | Recycled waste |
| Oil extracted by solvent extraction | 413 | Kg | |
| De-oiled seed cake | 2352 | Kg | |
| Hexane consumption in solvent extraction | 4.5 | Lit | |
| Crude oil fed to refinery | 1003 | Kg | |

TABLE 1-continued

Mass balance for the *Jatropha* seed biodiesel production process.

| Description | Quantity | Unit | Remarks |
|---|---|---|---|
| Bleaching earth used in oil refining | 20 | Kg | |
| Free fatty acid recovered in refining | 148 | Kg | |
| Refined oil taken directly for biodiesel | 847 | Kg | |
| Crude glycerine recycled to glycerolysis | 25 | Kg | Recycled waste |
| Pure glycerine taken to glycerolysis | 12 | Kg | |
| Fatty acid methyl ester product | 1014 | Kg | |
| Pure glycerine, 82-85% | 89 | Kg | |
| Yield of biodiesel from the original oil content of *Jatropha* seeds | 1.015 | Ratio | |

While we have described fundamental novel features of the invention, it will be understood that various omissions and substitutions and changes in the form and details may be possible without departing from the spirit of the invention. For example, it is expressly intended that all combinations of those elements and/or method steps, which perform substantially the same function in substantially the same way to achieve the same results, are within the scope of the invention.

The invention claimed is:

1. A method for obtaining seed oil suitable for use in producing fatty acid alkyl esters from seeds, comprising:
   cleaning the seeds;
   cracking the seeds;
   softening the seeds;
   extracting oil from the seeds, leaving a residual seed cake;
   degumming the extracted oil;
   bleaching the degummed extracted oil with bleaching earth, producing a first bleached oil sample and leaving spent bleaching earth;
   combining the residual seed cake and the spent bleaching earth;
   extracting oil remaining in the residual seed cake and the spent bleaching earth with a solvent;
   collecting the oil extracted from the oilseeds and the residual seed cake;
   degumming the collected oil;
   bleaching the degummed collected oil with bleaching earth, producing a second bleached oil sample; and
   combining the first bleached oil sample and the second bleached oil sample.

2. The method of claim 1, wherein the seeds are inedible oilseeds.

3. The method of claim 2, wherein the seeds are seeds of *Jatropha curcas*.

4. The method of claim 1, wherein the seeds are selected from the group consisting of soybean, canola, castor, coconut, corn, cotton, flax, hemp, jatropha, jajoba, mustard, sunflower, pongamia, copaiba, safflower, sesame, candlenut, petroleum nut, and neem.

5. The method of claim 1, wherein the seeds are softened by steaming.

6. The method of claim 5, wherein the seeds are steamed for at least 90 minutes.

7. The method of claim 5, wherein the steaming heats the seeds to a temperature of up to about 70° C.

8. The method of claim 1, wherein the oil is extracted from the seeds in an oil expander.

9. The method of claim 8, wherein oil is extracted from the cracked, softened seeds under high shear pressure.

10. The method of claim 1, wherein the solvent is hexane.

11. The method of claim 1, further comprising separating the extracted oil from the solvent in a flasher separator.

12. The method of claim 1, further comprising deaerating and deodorizing the collected oil.

13. The method of claim 1, further comprising refining the collected oil by distillation of fatty acids.

14. The method of claim 1, further comprising producing fatty acid alkyl esters from the collected oil.

15. The method of claim 14, wherein the fatty acid alkyl esters are produced from the collected oil through transesterification.

16. A method for producing fatty acid alkyl esters from oilseeds, comprising:
   cleaning oilseeds;
   cracking the oilseeds;
   softening the cracked oilseeds;
   extracting oil from the oilseeds, leaving a residual seed cake;
   degumming the extracted oil;
   bleaching the degummed extracted oil with bleaching earth, producing a first bleached oil sample and leaving spent bleaching earth;
   combining the residual seed cake and the spent bleaching earth;
   extracting oil remaining in the residual seed cake and spent bleaching earth with a solvent;
   collecting the oil extracted from the residual seed cake and spent bleaching earth;
   degumming the collected oil;
   bleaching the degummed collected oil with bleaching earth, producing a second bleached oil sample;
   combining the first bleached oil sample and the second bleached oil sample;
   refining the first and second bleached oil sample by distillation to remove free fatty acids from the oil;
   performing glycerolysis of the free fatty acids removed from the oil to produce monoglycerides, diglycerides and triglycerides;
   performing transesterification of the refined oil and monoglycerides, diglycerides and triglycerides produced by glycerolysis to produce fatty acid alkyl esters and glycerin; and
   separating the fatty acid alkyl esters and the glycerin produced by the transesterification reaction.

17. The method of claim 16, wherein the seeds are inedible oilseeds.

18. The method of claim 17, wherein the seeds are seeds of *Jatropha curcas*.

19. The method of claim 16, wherein the seeds are selected from the group consisting of soybean, canola, castor, coconut, corn, cotton, flax, hemp, jatropha, jajoba, mustard, sunflower, pongamia, copaiba, safflower, sesame, candlenut, petroleum nut, and neem.

20. The method of claim 16, wherein the oilseeds are softened by steaming.

21. The method of claim 16, wherein the free fatty acids are removed from the oil during refining with glycerin to produce monoglycerides, diglycerides and triglycerides.

22. The method of claim 16, wherein the transesterification further comprises contacting the refined oil and monoglycerides, diglycerides and triglycerides with an alcohol and a base.

23. The method of claim 22, wherein the alcohol is methanol.

24. The method of claim 22, wherein the base is selected from the group consisting of sodium hydroxide, potassium hydroxide, and sodium methoxide.

25. The method of claim 22, wherein the base is sodium methoxide.

26. The method of claim 16, wherein the transesterification further comprises:
- a first round of transesterification to produce fatty acid alkyl esters and glycerin,
- removing at least some of the glycerin produced in the first round of transesterification; and
- a second round of transesterification to produce additional fatty acid alkyl esters from unreacted oil, monoglycerides, diglycerides and triglycerides remaining after the first round of transesterification.

27. A method for purifying and reusing crude glycerin produced in a transesterification reaction, comprising:
- obtaining crude glycerin produced by a transesterification reaction, wherein the crude glycerin comprises glycerin, alcohol, and free fatty acid;
- removing at least some of the alcohol from the crude glycerin by a first flash distillation;
- separating at least some of the free fatty acid from the crude glycerin; and
- using the crude glycerin in a glycerolysis reaction to produce monoglycerides, diglycerides and triglycerides from free fatty acids.

28. The method of claim 27, further comprising a second flash distillation to remove additional alcohol from the glycerin following the separation of the free fatty acid from the glycerin.

29. The method of claim 26, wherein the glycerolysis reaction is conducted at a temperature between about 100° C. and 200° C.

30. The method of claim 26, further comprising combining the monoglycerides and diglycerides with triglycerides.

31. The method of claim 30, further comprising producing fatty acid alkyl esters from the combined monoglycerides, diglycerides, and triglycerides.

32. The method of claim 31, wherein the triglycerides are obtained from vegetable oil.

33. The method of claim 31, wherein the triglycerides are obtained from animal fats.

34. A method for recovering oil from spent bleaching earth, comprising:
- extracting spent bleaching earth with a solvent, wherein the spent bleaching earth comprises triglycerides from vegetable oils or animal fats;
- volatizing the solvent and triglycerides; and
- removing at least some of the solvent from the triglycerides in a flasher separator.

35. The method of claim 34, further comprising using the triglycerides to produce fatty acid alkyl esters.

36. The method of claim 35, wherein the fatty acid alkyl esters are produced from the recovered triglycerides in a transesterification reaction.

* * * * *